(12) United States Patent
Lewis et al.

(10) Patent No.: US 8,236,345 B2
(45) Date of Patent: Aug. 7, 2012

(54) COMPOSITION AND USE

(75) Inventors: Karen Lewis, Verona (IT); Nicola Jayne Lilliott, London (GB); Donald Colin MacKenzie, Harlow (GB)

(73) Assignee: SmithKline Beecham Limited, Brentford, Middlesex (GB)

( * ) Notice: Subject to any disclaimer, the term of this patent is extended or adjusted under 35 U.S.C. 154(b) by 690 days.

(21) Appl. No.: 11/779,546

(22) Filed: Jul. 18, 2007

(65) Prior Publication Data

US 2007/0275054 A1 Nov. 29, 2007

Related U.S. Application Data

(63) Continuation of application No. 10/130,229, filed as application No. PCT/GB00/04368 on Nov. 16, 2000, now abandoned.

(30) Foreign Application Priority Data

Nov. 16, 1999 (GB) .................................. 9927119.9
Nov. 16, 1999 (GB) .................................. 9927120.7
May 31, 2000 (GB) .................................. 0013236.5
May 31, 2000 (GB) .................................. 0013240.7

(51) Int. Cl.
*A61K 31/4436* (2006.01)
*A61K 31/4439* (2006.01)
*A61K 31/155* (2006.01)
*A61K 9/24* (2006.01)
*A61K 9/32* (2006.01)
*A61K 9/36* (2006.01)
*A61K 9/52* (2006.01)
*A61K 9/62* (2006.01)
*A61P 3/10* (2006.01)

(52) U.S. Cl. ........ 424/452; 424/455; 424/457; 424/458; 424/459; 424/461; 424/465; 424/469; 424/472; 424/474; 424/475; 424/480; 514/342; 514/635; 514/866; 514/960; 514/961; 514/962

(58) Field of Classification Search ............ 514/342, 514/369, 635, 866, 960, 961, 962; 424/452, 424/455, 457, 458, 459, 461, 465, 469, 472, 424/474, 475, 480
See application file for complete search history.

(56) References Cited

U.S. PATENT DOCUMENTS

| | | | |
|---|---|---|---|
| 4,999,226 A | 3/1991 | Schock et al. ................ 424/472 |
| 5,738,874 A | 4/1998 | Conte et al. .................. 424/472 |
| 5,965,584 A | 10/1999 | Ikeda et al. .................. 514/342 |
| 6,117,451 A | 9/2000 | Kumar .......................... 424/465 |
| 6,120,802 A | 9/2000 | Breitenbach et al. ......... 424/464 |
| 6,183,778 B1 | 2/2001 | Conte et al. .................. 424/472 |
| 6,296,874 B1 | 10/2001 | Cutie et al. ................... 424/474 |
| 6,403,121 B1 | 6/2002 | Adjei et al. ................... 424/468 |
| 6,451,342 B2 | 9/2002 | Adjei et al. ................... 424/474 |
| 6,461,639 B2 | 10/2002 | Adjei et al. ................... 424/472 |
| 6,475,521 B1 | 11/2002 | Timmins et al. .............. 424/469 |
| 6,495,162 B2 | 12/2002 | Cheng et al. .................. 424/464 |
| 6,524,621 B2 | 2/2003 | Adjei et al. ................... 424/490 |
| 6,660,300 B1 | 12/2003 | Timmins et al. .............. 424/469 |
| 6,780,432 B1 | 8/2004 | Cutie et al. ................... 424/468 |
| 2002/0004515 A1 | 1/2002 | Smith ........................... 514/342 |
| 2004/0102486 A1 | 5/2004 | Benincosa et al. ........... 514/342 |
| 2006/0263425 A1 | 11/2006 | Lewis et al. .................. 424/464 |
| 2008/0206336 A1 | 8/2008 | Coles et al. ................... 424/474 |

FOREIGN PATENT DOCUMENTS

| | | |
|---|---|---|
| AU | 734937 A | 9/1974 |
| JP | 5053521 | 9/1974 |
| JP | 08501544 | 2/1996 |
| WO | WO 94/06416 | 3/1994 |
| WO | WO 98/34614 | 8/1998 |
| WO | WO 98/57634 | 12/1998 |
| WO | WO 99/03477 | 1/1999 |
| WO | WO 99/47128 A1 | 9/1999 |
| WO | WO 00/27341 | 5/2000 |
| WO | WO 00/28989 | 5/2000 |
| WO | WO 00/28990 | 5/2000 |
| WO | WO 01/35940 | 5/2001 |

OTHER PUBLICATIONS

Gottlieb et al. *Annual Review of Medicine*, 49: 391-405 (1998).
GlaxoSmithKline: "Reply to examination report for Application No. 00976156", EPOLINE [Online], Oct. 10, 2003. Retrieved from the internet: URL: http://www.epoline.org/portal/public/registerplus> [retrieved on Mar. 7, 2007].
Remington's Pharmaceutical Sciences, Mack Pub. Co., Easton, PA, 18th ed., pp. 1633-1665 (1990).
JP Office Action Reporting letter, Oct. 15, 2010.

*Primary Examiner* — John Pak
(74) *Attorney, Agent, or Firm* — Kathryn A. Lutomski; John Lemanowicz

(57) ABSTRACT

A pharmaceutical composition, comprising a thiazolidinedione, such as Compound (I), metformin hydrochloride and a pharmaceutically acceptable carrier, wherein the thiazolidinedione and metformin hydrochloride are each dispersed within its own pharmaceutically acceptable carrier in the pharmaceutical composition and the use of such a composition in medicine.

17 Claims, No Drawings

COMPOSITION AND USE

This application is a continuation of application Ser. No. 10/130,229, filed Aug. 9, 2002, now abandoned, which is a 371 of International Application No. PCT/GB00/04368, filed Nov. 16, 2000.

This invention relates to novel compositions, in particular to compositions containing more than one active ingredient and their use in medicine, especially its use for the treatment of diabetes mellitus, preferably Type 2 diabetes, and conditions associated with diabetes mellitus.

Biguanide antihyperglycaemic agents are commonly used in the treatment of non-insulin dependent diabetes mellitus (NIDDM, or Type 2 diabetes). 1,1-Dimethylbiguanidine (or metformin) is an example of a biguanide antihyperglycaemic agent.

European Patent Application Publication Number 0 306 228 relates to certain thiazolidinedione derivatives disclosed as having antihyperglycaemic and hypolipidaemic activity. One particular thiazolidinedione disclosed in EP 0 306 228 is 5-[4-[2-(N-methyl-N-(2-pyridyl)amino)ethoxy]benzyl]thiazolidine-2,4-dione (hereinafter referred to as "Compound (I)"). European Patent 0 658 161 discloses certain salts of Compound (I) including the maleate salt at Example 1 thereof.

Compound (I) is an example of a class of anti-hyperglycaemic agents known as "insulin sensitisers". In particular Compound (I) is a thiazolidinedione insulin sensitiser.

The above mentioned publications are incorporated herein by reference.

An important consideration in the preparation of formulations containing a combination of active agents is the stability of the active agents given that mutual interaction of the agents themselves or the agents with excipients can lead to instability of the agents.

Metformin is most commonly administered in the form of its hydrochloride salt (or metformin HCl). It is indicated that in certain formulations Compound (I) is prone to decomposition, both during preparation and storage, due to the presence of metformin hydrochloride We now provide pharmaceutical compositions containing Compound (I) and metformin hydrochloride in which the instability of Compound (I) is inhibited or prevented.

Metformin hydrochloride is known to have poor inherent compressibility (U.S. Pat. No. 6,117,451). This lack of compressibility, when combined with the large unit dosage requirements of metformin hydrochloride (500 mg-1000 mg) results in significant formulation problems, especially in tablet formulation. The compressibility of metformin hydrochloride is usually improved by addition of a binding agent (or binder) which acts to bind the metformin hydrochloride particles into granules, the resultant granules having the flow and compressibility properties necessary for formulation.

In our hands we have found that polyvinyl pyrollidone (or PVP) is particularly effective as a binder for use with metformin hydrochloride providing excellent flow and compressibility properties. However it is indicated that the use of PVP in formulations which also contain Compound (I) destabilise Compound (I). It is also indicated that the particular methodology used to prepare the PVP/Compound (I) formulations has an impact upon the stability of Compound (I).

In response to these findings we now provide Compound (I) formulations containing PVP in which Compound (I) shows good stability. In addition the compositions containing metformin show good compressibility characteristics.

The above mentioned compositions are considered to be particularly useful for the formulation of Compound (I) especially in combination with metformin hydrochloride. It is believed that all thiazolidinediones would be subject to similar decomposition due to the presence of metformin hydrochloride and/or PVP.

Accordingly, in a first aspect the invention provides a pharmaceutical composition, comprising a thiazolidinedione, such as Compound (I), metformin hydrochloride and a pharmaceutically acceptable carrier, wherein the thiazolidinedione and metformin hydrochloride are each dispersed within its own pharmaceutically acceptable carrier in the pharmaceutical composition.

Suitably, the carrier for the thiazolidinedione, such as Compound (I), is different in composition to that of the carrier for metformin hydrochloride.

In one embodiment of the invention the thiazolidinedione and its carrier are substantially in admixture with the metformin hydrochloride and its carrier.

Suitably the thiazolidinedione and its carrier are substantially in homogenous admixture with the metformin hydrochloride and its carrier.

Suitably, the thiazolidinedione/carrier mixture is compacted with the metformin hydrochloride/carrier mixture in the composition, suitably to form a tablet. For example, the admixture of the thiazolidinedione/carrier mixture with the metformin hydrochloride/carrier mixture is compacted to form a tablet.

Preferably, the pre-formed thiazolidinedione/carrier mixture is admixed with the pre-formed metformin hydrochloride/carrier mixture on preparation of the composition of the invention. For example the thiazolidinedione/carrier mixture is admixed with the metformin hydrochloride/carrier mixture in a capsule form.

A suitable carrier for the thiazolidinedione comprises one or more components selected from: a binding agent, preferably other than PVP, a filler, a lubricants, a glidant, a disintegrant and a wetting agent.

Suitable carriers for the metformin hydrochloride comprises one or more components selected from: a binding agent, preferably PVP, a filler, a lubricants, a glidant, a disintegrant and a wetting agent.

The carrier for the metformin hydrochloride is as indicated preferably PVP but optionally at least one additional binder, for example hydroxypropylmethyl cellulose (or HPMC) is also used. In a particular preferred aspect when an additional binder or binders are used then the amount of PVP is the minimum required to provide the required compressability for metformin.

It is also envisaged that the thiazolidinedione and metformin hydrochloride can each be located in discrete zones with respect to each other, wherein each zone comprises the active agent and optionally a carrier.

Thus the invention also provides a pharmaceutical composition comprising a thiazolidinedione, such as Compound (I), metformin hydrochloride, and, optionally, a pharmaceutically acceptable carrier therefor, wherein the thiazolidinedione and metformin hydrochloride are located in discrete zones with respect to each other.

A layer provides a suitable zone, generally a compressed layer, of the active agent. Thus, the formulation may comprise layers, generally shaped layers of the active agents.

A suitable formulation is a tablet formulation. Thus one particular formulation is a multilayer tablet wherein the active agents are in separate layers. One particular formulation comprises a compressed form, for example a tablet, of one active agent formulated with a powdered form of the other active agent. The tablet and powder are generally encapsulated.

Preferably, the discrete zones are separated by a barrier layer, preferably an inert barrier layer. The barrier layer conveniently comprises a filler, such as lactose, and a lubricant, such as magnesium stearate.

The tablets containing active agents in discrete zones with respect to each other may be multilayer tablets. For example they may be bilayer tablets, where a layer of the granular form of one active agent is compressed, the granular form of the other active agent then added and compressed onto the layer of the first active agent. They may also be trilayer tablets prepared in an analogous manner.

As indicated, such compositions may conveniently be produced as tablets or capsules. Tablets may be produced by admixture of granular forms of the active agents followed by compression.

Granules of each active agent may be obtained by combination of the active agent with appropriate excipients, for example hydroxypropyl methyl cellulose, microcrystalline cellulose, sodium starch glycollate, lactose, and magnesium stearate, followed by granulation using conventional techniques.

Capsules may be produced by admixture of pelleted forms or granular forms of the active agents followed by encapsulation.

Pellets of each active agent may be obtained by combination of the active agent with appropriate excipients, for example microcrystalline cellulose and lactose, followed by pellet formation using conventional techniques. Granules are prepared as described herein. The production of tablets and capsules may be undertaken using techniques that are well known in the art.

Suitable dosages, preferably unit dosages, of thiazolidinediones such as Compound (I) and metformin hydrochloride include the known permissible doses for these compounds as described or referred to in reference texts such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

The dosages of each particular active agent in any given composition can as required vary within a range of doses known to be required in respect of accepted dosage regimens for that compound.

In one particular aspect, the composition comprises 2 to 12 mg of Compound (I).

Suitably the composition comprises 2, 3, 4, 5, 6, 7, 8, 9, 10, 11 or 12 mg of Compound (I).

Particularly, the composition comprises 2 to 4, 4 to 8, or 8 to 12 mg of Compound (I).

Particularly, the composition comprises 2 to 4 mg of Compound (I).

Particularly, the composition comprises 4 to 8 mg of Compound (I).

Particularly, the composition comprises 8 to 12 mg of Compound (I).

Preferably, the composition comprises 2 mg of Compound (I).

Preferably, the composition comprises 4 mg of Compound (I).

Preferably, the composition comprises 8 mg of Compound (I).

As indicated above the unit doses of metformin include those found in the reference texts mentioned herein and include the doses set out below.

A suitable dosage of metformin hydrochloride is between 100 to 3000 mg, for example 250, 500 mg, 850 mg, or 1000 mg.

Particular compositions of the invention comprise doses of Compound (I) in the range of from 2-12 mg and metformin hydrochloride in the range of from 100 to 3000 mg, for example 4 mg of Compound (I) and 500 mg of metformin hydrochloride. Other formulations comprise 2 mg of Compound (I) and 500 mg or 850 mg of metformin hydrochloride or 4 mg of Compound (I) and 850 mg of metformin hydrochloride.

Other thiazolidinediones include (+)-5-[[4-[(3,4-dihydro-6-hydroxy-2,5,7,8-tetramethyl-2H-1-benzopyran-2-yl)methoxy]phenyl]methyl]2,4-thiazolidinedione (or troglitazone), 5-[4-[(1-methylcyclohexyl)methoxy]benzyl]thiazolidine-2,4-dione (or ciglitazone), 5-[4-[2-(5-ethylpyridin-2-yl)ethoxy]benzyl]thiazolidine-2,4-dione (or pioglitazone) or 5-[(2-benzyl-2,3-dihydrobenzopyran]5-yl-methyl)thiazolidine-2,4-dione (or englitazone), especially 5-[4-[2-(5-ethylpyridin-2-yl)ethoxy]benzyl]thiazolidine-2,4-dione (or pioglitazone).

The compounds mentioned herein, in particular thiazolidinediones such as Compound (I), may exist in one of several tautomeric forms, all of which are encompassed by the invention as individual tautomeric forms or as mixtures thereof. The compounds mentioned herein may contain one or more chiral carbon atoms and hence can exist in two or more stereoisomeric forms, all of which are encompassed by the invention either as individual isomers or as mixtures of isomers, including racemates.

It will be understood that thiazolidinediones such as Compound (I) and metformin are in a pharmaceutically acceptable form, including pharmaceutically acceptable derivatives such as pharmaceutically acceptable salts, esters and solvates thereof, as appropriate to the relevant pharmaceutically active agent chosen. In certain instances herein the names used for the antidiabetic agent may relate to a particular pharmaceutical form of the relevant active agent. It will be understood that all pharmaceutically acceptable forms of the active agents per se are encompassed by this invention. Suitable pharmaceutically acceptable forms of thiazolidinediones such as Compound (I) and metformin include known pharmaceutically acceptable forms. Such derivatives are found or are referred to in standard reference texts such as the British and US Pharmacopoeias, Remington's Pharmaceutical Sciences (Mack Publishing Co.), The Extra Pharmacopoeia (London, The Pharmaceutical Press) (for example see the 31st Edition page 341 and pages cited therein) and the above mentioned publications. For example, a particular form of metformin is metformin hydrochloride.

Suitable pharmaceutically acceptable forms of Compound (I) include those described in EP 0 306 228 and WO 94/05659, especially pharmaceutically acceptable salted or solvated forms. A preferred pharmaceutically acceptable salt form of Compound (I) is a maleate. A preferred pharmaceutically acceptable solvated form of Compound (I) is a hydrate.

Metformin and metformin pharmaceutically acceptable forms are prepared according to known methods, such methods are found or are referred to in standard reference texts, such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or as described in the above mentioned publications.

Compound (I) or, a pharmaceutically acceptable salt thereof, or a pharmaceutically acceptable solvate thereof, may be prepared using known methods, for example those disclosed in EP 0 306 228 and WO 94/05659. The disclosures of EP 0 306 228 and WO 94/05659 are incorporated herein by reference.

It will be understood from the above that certain of the present compositions comprise a thiazolidinedione/carrier mixture substantially in admixture, suitably an homogenous admixture, with a metformin hydrochloride/carrier mixture.

The terms "admixture" and "mixture" are used interchangeably. When used herein the term "conditions associated with diabetes" includes those conditions associated with the pre-diabetic state, conditions associated with diabetes mellitus itself and complications associated with diabetes mellitus.

When used herein the term "conditions associated with the pre-diabetic state" includes conditions such as insulin resistance, including hereditary insulin resistance, impaired glucose tolerance and hyperinsulinaemia.

"Conditions associated with diabetes mellitus itself" include hyperglycaemia, insulin resistance, including acquired insulin resistance and obesity. Further conditions associated with diabetes mellitus itself include hypertension and cardiovascular disease, especially atherosclerosis and conditions associated with insulin resistance. Conditions associated with insulin resistance include polycystic ovarian syndrome and steroid induced insulin resistance and gestational diabetes.

"Complications associated with diabetes mellitus" includes renal disease, especially renal disease associated with Type 2 diabetes, neuropathy and retinopathy.

Renal diseases associated with Type 2 diabetes include nephropathy, glomerulonephritis, glomerular sclerosis, nephrotic syndrome, hypertensive nephrosclerosis and end stage renal disease.

As used herein the term "pharmaceutically acceptable" embraces both human and veterinary use. For example, the term "pharmaceutically acceptable" embraces a veterinarily acceptable compound.
When used herein "carrier" means "pharmaceutically acceptable carrier".

For the avoidance of doubt, unless otherwise stated, when reference is made herein to scalar amounts, including mg amounts, of the active compound such as Compound (I), in a pharmaceutically acceptable form, the scalar amount referred to is made in respect of the active compound per se. For example, 2 mg of Compound (I) in the form of the maleate salt is that amount of maleate salt, which provides 2 mg of Compound (I).

Diabetes mellitus is preferably Type 2 diabetes.

Glycaemic control may be characterised using conventional methods, for example by measurement of a typically used index of glycaemic control such as fasting plasma glucose or glycosylated haemoglobin (Hb A1c). Such indices are determined using standard methodology, for example those described in Tuescher A, Richterich, P., Schweiz. med. Wschr. 101 (1971), 345 and 390, and Frank P., "Monitoring the Diabetic Patent with Glycosolated Hemoglobin Measurements", Clinical Products 1988.

The compositions may be in the form of tablets, lozenges, suppositories, or capsules. Usually the compositions are adapted for oral administration. However, they may be adapted for other modes of administration, for example sublingual or transdermal administration.

In a further aspect the invention also provides a process for preparing a pharmaceutical composition comprising a thiazolidinedione, such as Compound (I), metformin hydrochloride, and a pharmaceutically acceptable carrier, in which the thiazolidinedione and metformin hydrochloride are each dispersed within its own pharmaceutically acceptable carrier, which process comprises:
(i) admixing the thiazolidinedione and a pharmaceutically acceptable carrier;
(ii) admixing the metformin hydrochloride and a pharmaceutically acceptable carrier; and
(iii) formulating the thiazolidinedione/pharmaceutically acceptable carrier mixture with the metformin hydrochloride/pharmaceutically acceptable carrier mixture.

Suitably, the carrier for the thiazolidinedione, such as Compound (I), has a different composition to that of the carrier for metformin hydrochloride. In one aspect of the process of the invention, step (iii) of the process includes substantially admixing the thiazolidinedione/carrier mixture with the metformin hydrochloride/carrier mixture, suitably to provide an homogenous mixture of the thiazolidinedione/carrier mixture with the metformin hydrochloride/carrier mixture.

The above mentioned process has a further advantage in that by pre-preparing the thiazolidinedione/carrier mixture and the metformin hydrochloride/carrier mixture it allows greater accuracy of dosing in the final composition, especially as in the case of Compound (I) compositions when there is a large differential between the thiazolidinedione and the metformin hydrochloride dosages.

In a further aspect of the process of the invention, for preparing a pharmaceutical composition comprising a thiazolidinedione/metformin hydrochloride composition wherein the thiazolidinedione and the metformin hydrochloride are located in discrete zones with respect to each other, step (iii) of the process, comprises formulating the thiazolidinedione/carrier mixture and the metformin hydrochloride/carrier mixture into discrete zones with respect to each other.

A suitable zone is provided by forming a layer, generally via compression, of the active agent. Thus the formulation comprise forming layers, generally shaped layers of each active agent. Alternatively, step (iii) of the process comprises formulating a compressed form, for example a tablet, of one active agent with a powdered form of the other active agent, providing for example a tablet and powder which may then be encapsulated according to normal practice for example in a capsule. For example a tabletted form of Compound (I) is Preferably, the discrete zones are separated by a barrier layer.

Tablets containing active agents in discrete zones with respect to each other are suitably formulate into multilayer tablets for example bilayer tablets. Such tablets are conveniently formed by compressing a granular form of one active agent, the granular form of the other active agent is then added and then compressed onto the layer of the first active agent. Trilayer tablets are prepared in an analogous manner.

Granules of the active agent/carrier mixture are prepared using standard methodology.

Preferably, the compositions are in unit dosage form. Unit dosage presentation forms for oral administration may be tablets, lozenges, or capsules and may as necessary contain conventional excipients such as binding agents, fillers, lubricants, glidants, disintegrants and wetting agents.

Examples of binding agents include acacia, alginic acid, carboxymethylcellulose calcium, carboxymethylcellulose sodium, dextrates, dextrin, dextrose, ethylcellulose, gelatin, liquid glucose, guar gum, hydroxyethyl cellulose, hydroxypropyl cellulose, hydroxypropyl methylcellulose, magnesium aluminium silicate, maltodextrin, methyl cellulose, polymethacrylates, polyvinylpyrrolidone, pregelatinised starch, sodium alginate, sorbitol, starch, syrup, and tragacanth.

Examples of fillers include calcium carbonate, calcium phosphate, calcium sulphate, carboxymethylcellulose calcium, carboxymethylcellulose sodium, compressible sugar, confectioner's sugar, dextrates, dextrin, dextrose, dibasic calcium phosphate dihydrate, dibasic calcium phosphate, fructose, glyceryl palmitostearate, glycine, hydrogenated vegetable oil-type 1, kaolin, lactose, maize starch, magnesium carbonate, magnesium oxide, maltodextrin, mannitol, microcrystalline cellulose, polymethacrylates, potassium chloride, powdered cellulose, pregelatinised starch, sodium chloride, sorbitol, starch, sucrose, sugar spheres, talc, tribasic calcium phosphate, and xylitol.

Examples of lubricants include calcium stearate, glyceryl monostearate, glyceryl palmitostearate, magnesium stearate, microcrystalline cellulose, sodium benzoate, sodium chloride, sodium lauryl sulphate, stearic acid, sodium stearyl fumarate, talc, and zinc stearate.

Examples of glidants include colloidal silicon dioxide, powdered cellulose, magnesium trisilicate, silicon dioxide, and talc.

Examples of disintegrants include alginic acid, carboxymethylcellulose calcium, carboxymethylcellulose sodium, colloidal silicon dioxide, croscarmellose sodium, crospovidone, guar gum, magnesium aluminium silicate, microcrystalline cellulose, methyl cellulose, polyvinylpyrrolidone, polacrilin potassium, pregelatinised starch, sodium alginate, sodium lauryl sulphate, and sodium starch glycollate.

An example of a pharmaceutically acceptable wetting agent is sodium lauryl sulphate.

As required the compositions may be prepared by conventional methods of blending, tabletting, or encapsulation. Repeated blending operations may be used to distribute the active agent throughout those compositions employing large quantities of fillers. Such operations are of course conventional in the art. The tablets may be coated according to methods well known in normal pharmaceutical practice.

Compositions may, if desired, be in the form of a pack accompanied by written or printed instructions for use.

No adverse toxicological effects are expected for the compositions of the invention in the above mentioned dosage ranges.

The following examples illustrate the invention but do not limit it in any way.

EXAMPLES a) Preparation of Metformin HCl Granules

Example 1

Metformin HCl Granules

Metformin HCl is granulated with Polyvinyl pyrollidone and the resultant granule dried and lubricated.

| Composition of Metformin HCl granule | mg |
|---|---|
| Metformin HCl | 500 |
| Polyvinyl pyrollidone | 15 or 20 |
| Magnesium stearate | 5 |

Example 2

Metformin HCl High Shear Granulation

Metformin HCl is dry-blended with PVP and hydroxypropyl methylcellulose. The resultant mixture is wet granulated with purified water in a high shear mixer granulator. The wet granules are then screened, dried in a fluid bed drier and the dried granules are passed through a further screen.

| Composition of Metformin HCl granule | mg |
|---|---|
| Metformin HCl | 500 |
| Polyvinyl pyrollidone | 5-20 |
| HPMC | 20-30 |

Example 3

Metformin HCl Spray Granulation

Metformin HCl is dry blended with syloid then spray granulated with a solution of aqueous polyvinyl pyrollidone. The resultant granule is screened.

| Composition of Metformin HCl granule | mg |
|---|---|
| Metformin HCl | 500 |
| Polyvinyl pyrollidone | 10-25 |
| Syloid | 2.5-25 | b) Preparation of Metformin HCl Pellets

Example 4

Metformin HCl Pellets

Metformin HCl, microcrystalline cellulose and lactose are blended then water added to wet. The wet mass is extruded and spheronised to give pellets. The pellets are then dried.

| Composition of Metformin HCl pellets | mg |
|---|---|
| Metformin HCl | 500 |
| Microcrystalline cellulose | 75 |
| Lactose | 50 | c) Preparation of Granules of Compound (I) Maleate Salt

Example 5

Granules of Compound (I)

Compound (I) hydroxypropyl methylcellulose, microcrystalline cellulose sodium starch glycollate and lactose are blended then wet granulated. The resultant granules are screened dried and further screened.

| Composition) | mg |
|---|---|
| Compound (I) | 5.3 |
| Hydroxypropyl methyl cellulose | 3.7 |
| Microcrystalline cellulose | 30.0 |
| Sodium starch glycolate | 7.5 |
| Lactose | 102 |
| Magnesium stearate | 1.5 |

Example 6

Granules of Compound (1)

| Composition | mg |
|---|---|
| Compound (I) (e.g. for 4 mg of compound (1)) | 5.3 |
| Hydroxypropyl methyl cellulose | 3.7 |
| Microcrystalline cellulose | 30.0 |
| Sodium starch glycolate | 7.5 |
| Lactose | 102 |

Example 7

Granules of Compound (I) Maleate Salt (Bilayer)

Compound (I) hydroxypropyl methylcellulose, microcrystalline cellulose sodium starch glycollate and lactose are blended then wet granulated. The resultant granules are screened dried and further screened, then blended with magnesium stearate.

| Composition of granules | mg |
|---|---|
| Compound (I) (eg equivalent to 4 mg compound I) | 5.3 |
| Hydroxypropyl methyl cellulose | 7.0 |
| Microcrystalline cellulose | 48.0 |
| Sodium starch glycolate | 13.75 |
| Lactose | 198.20 |
| Magnesium stearate | 1.38-2.75 |

Example 8

Granules of Compound (I) Maleate Salt (Press Coat)

Prepared as in example 7 above.

| Composition of granules | mg |
|---|---|
| Compound (I) | 5.3 |
| Hydroxypropyl methyl cellulose | 7.5 |
| Microcrystalline cellulose | 60.0 |
| Sodium starch glycolate | 15.0 |
| Lactose | 238.9 |
| Magnesium stearate | 3.3 |

Example 9

Granular Concentrate of Compound (I) Maleate Salt

Granules of each active agent, which include conventional binders, diluents, lubricants and glidants where appropriate, are compressed into a tablet.

| Concentrate Granules of Compound (I) | mg |
|---|---|
| Compound (I) | 5.3 |
| Hydroxypropyl methyl cellulose | 2.0 |
| Microcrystalline cellulose | 8.0 |
| Sodium starch glycolate | 2.0 |
| Lactose | 22.7 |

Example 10

Granular Concentrate of Compound (I) Maleate Salt

Approximately two thirds of the lactose monohydrate is passed through a suitable screen and blended with the milled maleate salt of Compound (I). Sodium starch glycollate, hydroxypropyl methylcellulose, microcrystalline cellulose and the remaining lactose are passed through a suitable screen and added to the mixture. Blending is then continued. The resulting mixture is then wet granulated with purified water. The wet granules are then screened, dried on a fluid bed drier and the dried granules are passed through a further screen and finally homogenised.

| Composition of granular concentrate | |
|---|---|
| Ingredient | Quantity (%) |
| Milled Compound (I) as maleate salt | 13.25 (pure maleate salt) |
| Sodium Starch Glycollate | 5.00 |
| Hydoxypropyl Methylcellulose 2910 | 5.00 |
| Microcrystalline Cellulose | 20.0 |
| Lactose Monohydrate, regular grade | to 100 |
| Purified water | * |

* Removed during processing.

Example 11

Compression Blend of Compound (I) Maleate Salt

The granules from Example 10 are placed into a tumble blender. Approximately two thirds of the lactose is screened and added to the blender. The microcrystalline cellulose, sodium starch glycollate, magnesium stearate and remaining lactose are screened and added to the blender and the mixture blended together.

| Composition of compression blend | | | |
|---|---|---|---|
| | Quantity (mg per dosage form) | | |
| Tablet Strength | 1.0 mg | 2.0 mg | 4.0 mg |
| Active Ingredient: | | | |
| Compound (I) maleate Concentrate granules from example 10 | 10.00 | 20.00 | 40.00 |
| Other Ingredients: | | | |
| Sodium Starch Glycollate | 6.96 | 6.46 | 5.46 |
| Microcrystalline Cellulose | 27.85 | 25.85 | 21.85 |
| Lactose monohydrate | 104.44 | 96.94 | 81.94 |
| Magnesium Stearate | 0.75 | 0.75 | 0.75 |

Example 12

Tablets of Compound (I) Maleate Salt

| Composition | mg |
|---|---|
| Compound I | 5.3 |
| Hydroxypropyl methyl cellulose | 2.5-5.0 |
| Microcrystalline cellulose | 20.0 |
| Sodium starch glycolate | 5.0 |
| Lactose | 66.2 |
| Magnesium stearate | 1.0 |

Example 13

Tablets of Compound 1

The compression blend produced as in example 11 is compressed on a rotary tablet press to a target weight of 150 mg for the 1, 2 and 4 mg tablets and to a target weight of 300 mg for the 8 mg tablets.

The tablet cores are then transferred to a tablet coating machine, pre-warmed with warm air (approximately 65° C.) and film coated until the tablet weight has increased by 2.0% to 3.5%.

| Composition of tablets of Compound (I) maleate salt | | | | |
|---|---|---|---|---|
| | Quantity (mg per Tablet) | | | |
| Tablet Strength | 1.0 mg | 2.0 mg | 4.0 mg | 8.0 mg |
| Active Ingredient: | | | | |
| Compound (I) maleate Concentrate granules from Example 10 | 10.00 | 20.00 | 40.00 | 80.00 |
| Other Ingredients: | | | | |
| Sodium Starch Glycollate | 6.96 | 6.46 | 5.46 | 10.92 |
| Microcrystalline Cellulose | 27.85 | 25.85 | 21.85 | 43.70 |
| Lactose monohydrate | 104.44 | 96.94 | 81.94 | 163.88 |
| Magnesium Stearate | 0.75 | 0.75 | 0.75 | 1.50 |
| Total Weight of Tablet Core | 150.0 | 150.0 | 150.0 | 300.0 |
| Aqueous film coating material | 4.5 | 4.5 | 4.5 | 9.0 |
| Total Weight of Film Coated Tablet | 154.5 | 154.5 | 154.5 | 309.0 | d) Preparation of Pellets of Compound (I) Maleate Salt

Compound (I), microcrystalline cellulose and lactose are blended then water added. The wet mass is extruded and spheronised to give pellets. The pellets are dried.

Example 14

Pellets of COMPOUND (I)

| Composition of pellets | mg |
|---|---|
| Compound (I) | 5.3 |
| Microcrystalline cellulose | 25.0 |
| Lactose | 19.7 | e) Preparation of Compound (I) Maleate Salt/Metformin HCl Tablets (i) Direct Compression Metformin HCl granules and either Compound (I) maleate salt granules or Compound (I) maleate salt compression blends are mixed in the appropriate ratio to give the desired tablet strength of combination tablet with microcrystalline cellulose and magnesium stearate. The final compression blend is compressed into tablets and aqueous film coated.

Example 15

Compound (I) Maleate Salt/Metformin HCl Tablets

| Tablet Formula | mg/tablet |
|---|---|
| Granules of Compound (I) (equivalent to 4 mg pfb) (see example 5) | 150 |
| Granules of metformin HCl, see example 1 (equivalent to 500 mg metformin HCl) | 520 or 525 |

Example 16

Compound (I) Maleate Salt/Metformin HCl Tablets

| Tablet Formula | mg/tablet |
|---|---|
| Granules of Compound (I) (equivalent to 4 mg pfb) (see example 9) | 40 |
| Granules of metformin HCl (equivalent to 500 mg metformin HCl) (see example 1) | 525 |

Example 17

Compound (I) Maleate Salt/Metformin HCl Tablets

| Tablet formula | Amount % |
|---|---|
| Metformin HCl granules (examples 1, 2 or 3) (equivalent to 500 mg Metformin HCl) | As required |
| Compound (I) maleate salt granules) (examples 5, 6, 9, 10, 11 (equivalent to 1, 2 or 4 mg Compound (I)) | As required |
| Microcrystalline cellulose | 4-7% |
| Magnesium stearate | 0.5% |

Example 18

Compound (I) Maleate Salt/Metformin HCl Tablets

| Tablet formula | Amount % |
|---|---|
| Metformin HCl granules (examples 1, 2 or 3) (equivalent to 500 mg Metformin HCl) | As required |
| Compound (I) maleate salt granules (examples 5, 6, 9, 10, 11) (equivalent to 1, 2 or 4 mg Compound (I)) | As required |
| Hydroxypropyl methylcellulose | 4-7% |
| Magnesium stearate | 0.5% |

(ii) Mixed Pellets or Granules in a Capsule

Pellets or granules of Compound (I) and metformin HCl are combined, lubricated and filled into a hard gelatin capsule.

Example 19

Mixture of Pellets

| Composition | mg/capsule |
|---|---|
| Pellets of Compound (I) (example 14, e.g. equiv. to 4 mg) | 50 |
| Pellets of metformin HCl (example 4) (equivalent to 500 mg metformin HCl) | 625 |

Example 20

Mixture of Pellets

| Composition | mg/capsule |
|---|---|
| Pellets of Compound (I) (example 14, e.g. equiv. to 4 mg) | 50 |
| Pellets of metformin HCl (example 4) (equivalent to 500 mg metformin HCl) | 625 |
| Magnesium stearate | 3.4 |

Example 21

Mixture of Granules

| Composition | Amount |
|---|---|
| Metformin HCl granules (examples 1, 2, 3) (equivalent to 500 mg Metformin HCl) | As required |
| Compound (I) maleate salt granules (examples 5, 6, 9, 10, 11) (equivalent to 1, 2 or 4 mg Compound (I)) | As required |
| Magnesium stearate | 0.5% |

(iii) Encapsulation of Tablet of Compound (I) Maleate Salt

A tablet of Compound (I) maleate salt of the desired strength, example 7, is filled into an appropriate sized capsule shell and overfilled with metformin hydrochloride (blended with magnesium stearate) or a Metformin HCl granule, see example 1 or 2, equivalent to 500 mg.

Example 22

Compound (I) Maleate Salt/Metformin HCl Capsule

| Composition | mg/capsule |
|---|---|
| Tablet of Compound (I) maleate salt (example 12) (equivalent 4 mg Compound (I)) | 150 |
| Metformin hydrochloride | 500 mg |

Example 23

Compound (I) Maleate Salt/Metformin HCl Capsule

| Composition | mg/capsule |
|---|---|
| Tablet of Compound (I) maleate salt (example 12, 13) (equivalent to 1, 2 or 4 mg Compound (I)) | 1 tablet |
| Metformin hydrochloride | 500 mg |
| Magnesium stearate | 2.5 mg |

Example 24

Compound (I) Maleate Salt/Metformin HCl Capsule

| Composition | Amount |
|---|---|
| Tablet of Compound (I) maleate salt (example 12, 13) (equivalent to 1, 2 or 4 mg Compound (I)) | 1 tablet |
| Metformin HCl granules (examples 1, 2, 3) (equivalent to 500 mg Metformin HCl) | As required |

(iv) Bi and Tri Layer Tablets

Granules of metformin hydrochloride and Compound (I) are compressed as descrete layers to form a bilayer tablet.

Granules of metformin hydrochloride and Compound (I) are compressed as descrete layers that are separated by a barrier layer to form a trilayer tablet.

Example 25

A Bilayer Tablet

| Bilayer tablet composition | Amount (mg) |
|---|---|
| Metformin HCl granules (examples 1, 2 or 3) (equivalent to 500 mg Metformin HCl) | 520-540 |
| Compound (I) maleate salt granules (examples 7 or 5, 6, 9, 10, 11) (equivalent to 1, 2 or 4 mg Compound (I)) | 275 |

Example 26

A Trilayer Tablet

| Barrier layer (non active) | mg |
|---|---|
| Lactose | 198 |
| magnesium stearate | 1-2 |

| Trilayer tablet formulation | Amount (mg) |
|---|---|
| Metformin HCl granules (examples 1, 2 or 3) (equivalent to 500 mg Metformin HCl) | 520-540 |
| Barrier layer | 200 |
| Compound (I) maleate salt granules (examples 8 or 5, 6, 9, 10, 11) (equivalent to 1, 2 or 4 mg Compound (I)) | 275 |

(v) Press Coated Tablets

Compound (I) is applied by a press coating procedure around a pre formed Metformin HCl tablet, or, Metformin hydrochloride is applied by a press coating procedure around a pre formed tablet of Compound (I)

Example 27

Press Coated Tablet; Compound (I) Maleate Salt as Press Coat

A granule of compound I equivalent to 1 mg, 2 mg or 4 mg of Compound (I) maleate salt is press coated onto a preformed metformin hydrochloride tablet
Metformin HCl Tablet 500 ml
(formed by blending granules of metformin Hydrochloride prepared as in examples 1, 2 or 3 with magnesium stearate, then compressing into tablets)

| Formula | mg/tablet |
|---|---|
| Metformin HCl tablet (equivalent to 500 mg metformin hydrochloride) | 520-540 |
| Press coat of Compound (I) maleate salt, example 8 (equivalent to 4 mg Compound (I)) | 330 |

Example 28

Press Coated Tablet; Metformin Hydrochloride as Press Coat

A granule of metformin hydrochloride, equivalent to 500 mg is press coated onto a pre formed tablet of Compound (I) maleate salt, see example 13

| Formula | mg/tablet |
|---|---|
| Tablet of Compound (I) maleate salt (equivalent to 1, 2 or 4 mg Compound 1) | 154.5 |
| Metformin hydrochloride granule, example 1, 2 (equivalent to 500 mg metformin hydrochloride) | 535 |
| Magnesium stearate | 2.7 |

The invention claimed is:

1. A pharmaceutical composition comprising a thiazolidinedione dispersed in a first pharmaceutically acceptable carrier and metformin hydrochloride dispersed in a second pharmaceutically acceptable carrier, wherein:
   the thiazolidinedione is 5-[4-[2-(N-methyl-N-(2-pyridyl)amino)ethoxy]benzyl]thiazolidine-2,4-dione, or a tautomer thereof, in a pharmaceutically acceptable form,
   the first carrier consists essentially of hydroxypropyl methyl cellulose, microcrystalline cellulose, sodium starch glycollate, and lactose; and
   the second carrier consists essentially of polyvinyl pyrolidone and hydroxypropyl methyl cellulose.

2. A composition according to claim 1, which comprises 2 mg of said 5-[4-[2-(N-methyl-N-(2-pyridyl)amino)ethoxy]benzyl]thiazolidine-2,4-dione, or a tautomer thereof, in a pharmaceutically acceptable form.

3. A composition according to claim 1, which comprises 4 mg of said 5-[4-[2-(N-methyl-N-(2-pyridyl)amino)ethoxy]benzyl]thiazolidine-2,4-dione, or a tautomer thereof, in a pharmaceutically acceptable form.

4. A composition according to claim 1, wherein the composition comprises 500 mg of metformin hydrochloride.

5. A composition according to claim 1, wherein the composition comprises 1000 mg of metformin hydrochloride.

6. A composition according to claim 1, wherein said pharmaceutically acceptable form is a maleate salt.

7. A composition according claim 1, wherein said pharmaceutically acceptable form is a hydrate.

8. A composition according to claim 1, wherein said pharmaceutically acceptable form is a hydrate of a maleate salt.

9. A composition according to claim 1, wherein the thiazolidinedione/first carrier dispersion is substantially in homogenous admixture with the metformin hydrochloride/second carrier dispersion.

10. A composition according to claim 1, wherein the thiazolidinedione/first carrier dispersion is compacted with the metformin hydrochloride/second carrier dispersion in the composition.

11. A composition according to claim 1, wherein the composition is in the form of a tablet.

12. A composition according to claim 1, wherein the thiazolidinedione/first carrier dispersion and metformin hydrochloride/second carrier dispersion are located in discrete zones with respect to each other in the composition.

13. A composition according to claim 12, in the form of a multilayer tablet, wherein the thiazolidinedione/first carrier dispersion and the metformin hydrochloride/second carrier dispersion are in separate layers.

14. A composition according to claim 12, wherein the discrete zones are separated by a barrier layer.

15. A composition according to claim 14, wherein the barrier layer comprises a filler and a lubricant.

16. A composition according to claim 12, wherein one zone is a compressed layer and the other is in a powder form.

17. A composition according to claim 16, wherein the compressed layer is a tablet and the tablet and powder are encapsulated in a capsule form.

* * * * *